United States Patent
Lee et al.

(10) Patent No.: US 10,435,682 B2
(45) Date of Patent: Oct. 8, 2019

(54) ARGININE DEIMINASE GENE THERAPY FOR DISORDERED PROTEINS

(71) Applicant: University of South Florida, Tampa, FL (US)

(72) Inventors: Daniel C. Lee, Tampa, FL (US); Kevin Ron Nash, Seffner, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/438,556

(22) Filed: Feb. 21, 2017

(65) Prior Publication Data

US 2017/0240880 A1    Aug. 24, 2017

Related U.S. Application Data

(60) Provisional application No. 62/297,488, filed on Feb. 19, 2016.

(51) Int. Cl.
| | |
|---|---|
| *C12N 9/99* | (2006.01) |
| *C12N 9/78* | (2006.01) |
| *A61K 38/00* | (2006.01) |

(52) U.S. Cl.
CPC ........ *C12N 9/78* (2013.01); *C12Y 305/03006* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach | |
| 4,920,016 A | 4/1990 | Allen et al. | |
| 4,921,757 A | 5/1990 | Wheatley et al. | |
| 5,994,136 A | 11/1999 | Naldini et al. | |
| 6,013,516 A | 1/2000 | Verma et al. | |
| 6,635,462 B1 | 10/2003 | Ensor et al. | |
| 8,663,967 B2 | 3/2014 | Huang et al. | |

OTHER PUBLICATIONS

Mohlake, Peter et al., "Arginine Metabolising Enzymes as Therapeutic Tools for Alzheimers' Disease: Peptidyl Arginine Deiminase Catalyses Fibrillogenesis of B-amyloid Peptides", Springer Science + Business Media, LLC, (2010), 41: 149-158, Human Press.
Whiteley, Chris G., "Arginine metabolising enzymes as targets against Alzheimers' disease", Neurochemistry International 67 (2014) 23-31, Graduate Institute of Applied Science & Technology, National Taiwan University of Science and Technology, Taipei, Taiwan.
Lin, Shan-Erh et al., "Depletion of Arginine by Recombinant Arginine Deiminase Induces nNOS-Activated Neurotoxicity in Neuroblastoma Cells", BioMed Research International, (2014), vol. 2014, Article ID 589424, 8 pages, Hindawi Publishing Corporation.
Kyte et al., "A Simple Method for Displaying the Hydropathic Character of a Protein", J Mal. Biol., (1982), vol. 157, pp. 105-132.
Heagerty, Patrick J. et al., "Time-Dependent ROC Curves for Censored Survival Data and a Diagnostic Marker", Biometrics, (Jun. 2000), vol. 56, pp. 337-344, Department of Biostatistics, University of Washington, Seattle, WA.
Liberman, H. A and Lachman, L., Eds., Pharmaceutical Dosage Forms, Marcel Decker, New York, NY. (1980).
Zufferey et al., "Multiply attenuated lentiviral vector achieves afficient gene delivery in vivo", Nature Biotechnology, Sep. 1997, vol. 15, pp. 871-874.
Naldini et al., "Efficient transfer, integration, and sustained long-term expression of the transgene in adult rat brains injected with a lentiviral vector", Proc. Natl. Acad. Sci., Oct. 1996, vol. 93, pp. 11382-11388.
Blomer et al., "Highly Efficient and Sustained Gene Transfer in Adult Neurons with a Lentivirus Vector", Journal of Virology, Sep. 1997, pp. 6641-6649.
Hoover, John E., Remington's Pharmaceutical Sciences, Mack Publishing Co., Easton, Pa. (1975).

*Primary Examiner* — Hope A Robinson
(74) *Attorney, Agent, or Firm* — Meunier Carlin & Curfman LLC

(57) ABSTRACT

The invention relates to compositions comprising arginine deiminase and their use in a method of reducing aggregation of disordered protein in a subject.

8 Claims, 19 Drawing Sheets
(13 of 19 Drawing Sheet(s) Filed in Color)
Specification includes a Sequence Listing.

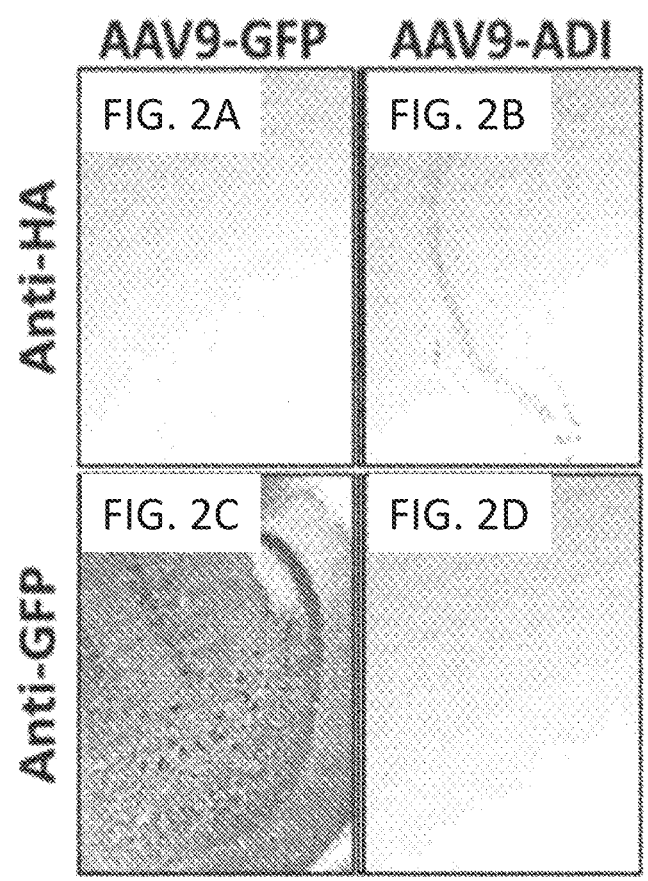

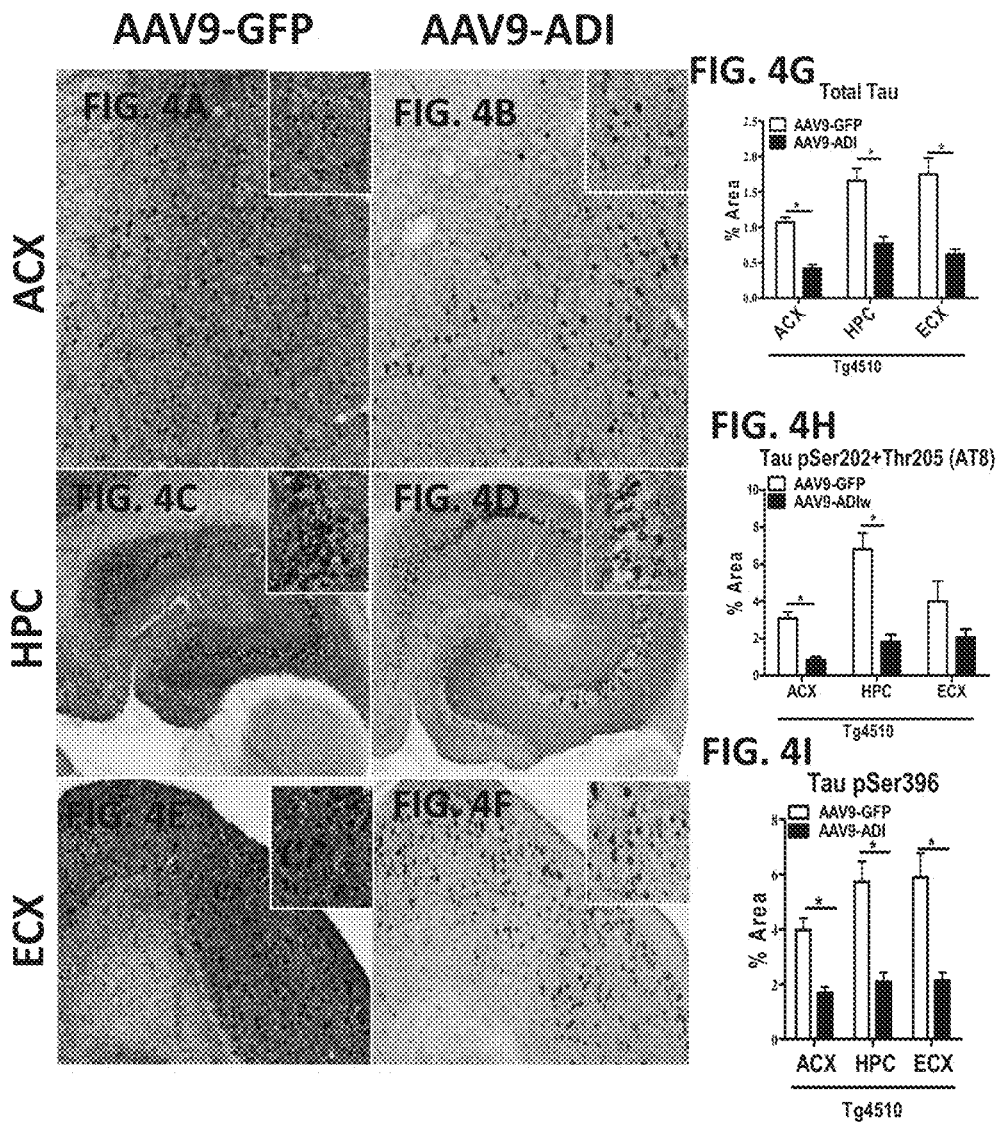

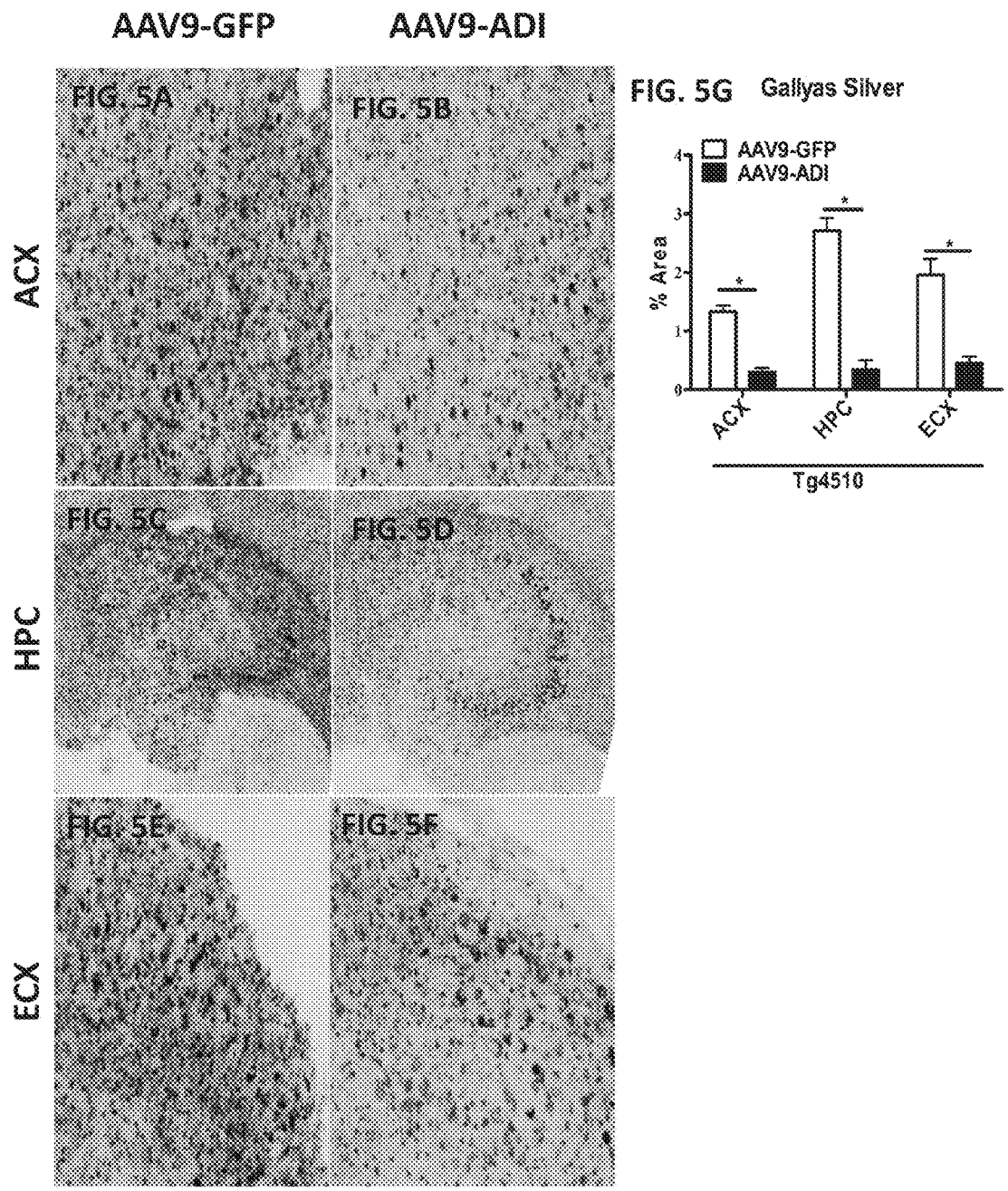

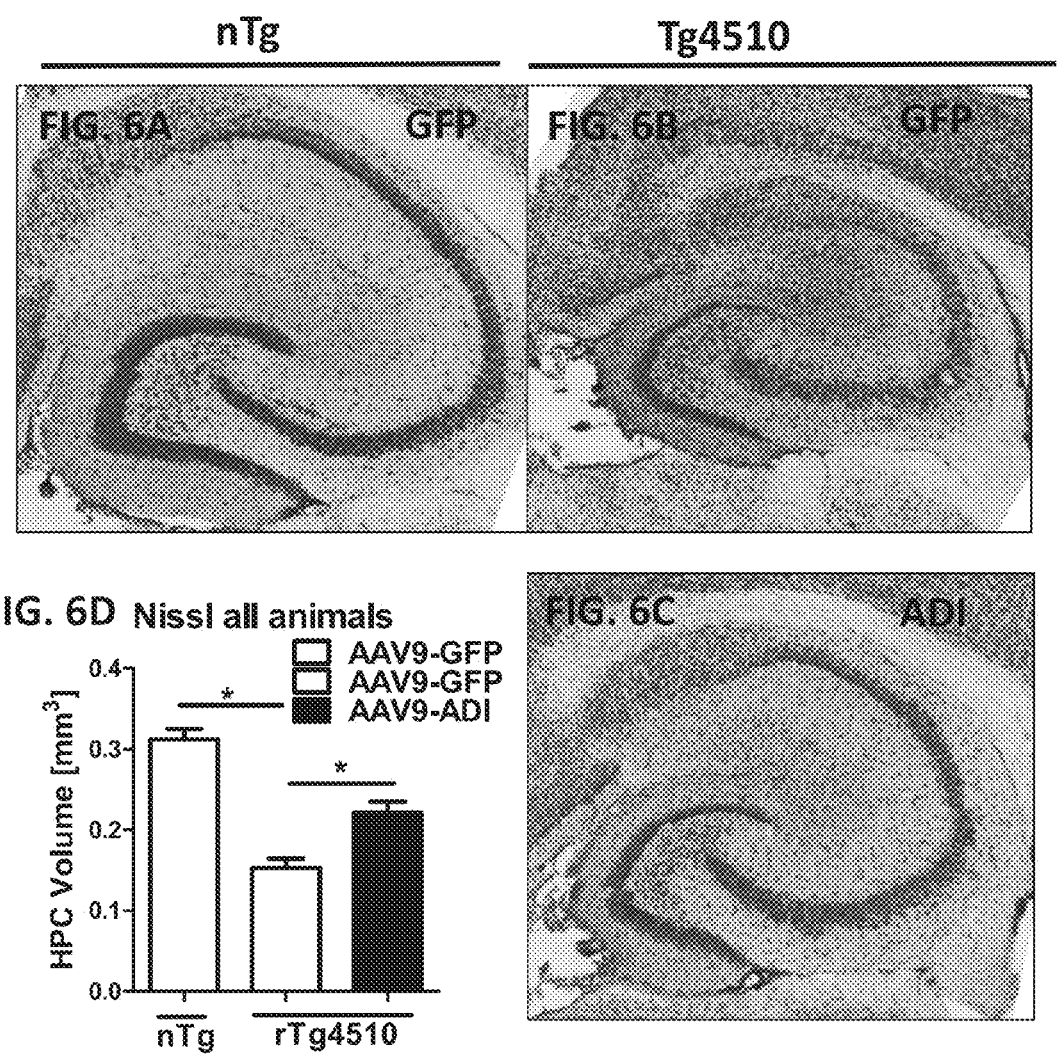

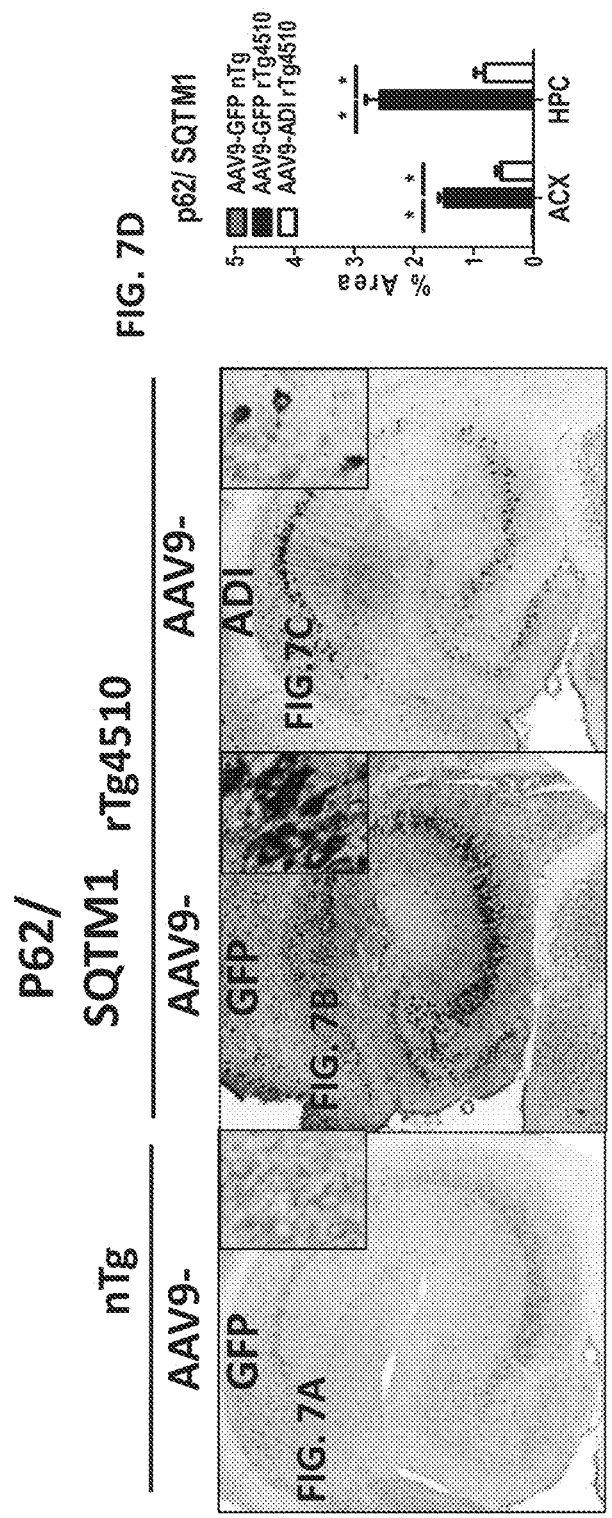

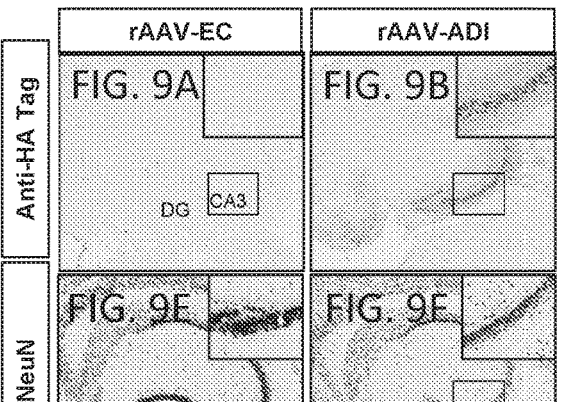

ATGTCTGTATTTGACAGTAAATTTAAAGGAATTCACGTTTATTCAGAAATTGGTGAA
TTAGAATCAGTTCTAGTTCACGAACCAGGACGCGAAATTGACTATATTACACCAGCT
AGACTAGATGAATTATTATTCTCAGCTATCTTAGAAAGCCACGATGCTAGAAAAGAA
CACAAACAATTCGTAGCAGAATTAAAAGCAAACGACATCAATGTTGTTGAATTAATT
GATTTAGTTGCTGAAACATATGATTTAGCATCACAAGAAGCTAAAGATAAATTAATC
GAAGAATTTTTAGAAGACTCAGAACCAGTTCTATCAGAAGAACACAAAGTAGTTGT
AAGAAACTTCTTAAAAGCTAAAAAAACATCAAGAAAATTAGTAGAAATCATGATGG
CAGGGATCACAAAATACGATTAGGTATCGAAGCAGATCACGAATTAATCGTTGAC
CCAATGCCAAACCTATACTTCACACGTGACCCATTTGCATCAGTAGGTAATGGTGTA
ACAATCCACTACATGCGTTACAAAGTTAGACAACGTGAAACATTATTCTCAAGATTT
GTATTCTCAAATCACCCTAAACTAATTAACACTCCATGATACTACGACCCTTCACTA
AAATTATCAATCGAAGGTGGAGACGTATTTATCTACAACAATGACACATTAGTAGTT
GGTGTTTCTGAAAGAACTGACTTACAAACAGTTACTTTATTAGCTAAAAACATTGTT
GCTAATAAAGAATGTGAATTCAAACGTATTGTTGCAATTAACGTTCCAAAATGAACA
AACTTAATGCACTTAGACACATGACTAACAATGTTAGACAAGGACAAATTCCTATAC
TCACCAATCGCTAACGACGTATTTAAATTCTGAGATTATGACTTAGTAAACGGTGGA
GCAGAACCACAACCAGTTGAAAACGGATTACCTCTAGAAGGATTATTACAATCAAT
CATTAACAAAAAACCAGTTTTAATTCCTATCGCAGGTGAAGGTGCTTCACAAATGGA
AATCGAAAGAGAAACACACTTCGATGGTACAAACTACTTAGCAATTAGACCAGGTG
TTGTAATTGGTTACTCACGTAACGAAAAAACAAACGCTGCTCTAGAAGCTGCAGGC
ATTAAAGTTCTTCCATTCCACGGTAACCAATTATCATTAGGTATGGGTAACGCTCGTT
GTATGTCAATGCCTTTATCACGTAAAGATGTTAAGTGATAG (SEQ ID NO: 1)

FIG. 12

ATGTCGGTGTTTGATTCAAAGTTCAAAGGAATCCACGTGTACTCAGAAATTGGCGAG
CTCGAAAGCGTGCTGGTGCACGAACCCGGAAGAGAGATCGACTATATCACTCCAGC
GCGCCTGGATGAACTGCTGTTCTCGGCCATCTTGGAATCGCATGACGCACGCAAGGA
ACACAAGCAATTTGTCGCCGAACTTAAAGCCAATGACATCAATGTGGTCGAACTGAT
TGACCTGGTCGCGGAAACCTACGATCTGGCGAGCCAGGAAGCCAAAGATAAGCTCA
TCGAGGAGTTTTTGGAGGACAGCGAACCAGTGCTCTCCGAAGAACATAAGGTCGTG
GTGAGGAATTTCCTCAAAGCTAAAAAGACTTCCCGGAAGCTGGTGGAGATTATGAT
GGCTGGCATCACCAAATACGATCTTGGCATCGAGGCCGACCACGAGCTGATCGTCG
ATCCTATGCCGAATCTGTACTTTACCCGCGACCCCTTCGCCTCGGTCGGAAATGGGG
TGACTATCCACTACATGCGCTACAAAGTCAGACAACGGGAAACCCTCTTCTCCCGGT
TCGTGTTCTCCAACCATCCGAAGCTGATCAACACCCCTTGGTACTACGACCCATCAC
TGAAGCTCTCCATCGAAGGCGGTGACGTGTTCATCTACAACAATGATACCCTCGTGG
TGGGCGTGTCAGAGCGGACCGACTTGCAAACTGTGACCCTTCTGGCTAAGAACATCG
TGGCAAACAAAGAGTGCGAGTTCAAGCGCATCGTCGCTATCAACGTCCCGAAGTGG
ACGAACCTCATGCACCTTGACACCTGGCTGACGATGTTGGACAAAGACAAGTTCCTC
TACTCCCCGATTGCAAACGATGTGTTCAAGTTTTGGGATTACGACTTGGTGAACGGA
GGAGCCGAGCCACAGCCAGTGGAGAACGGACTGCCCCTCGAAGGACTGCTGCAGAG
CATCATCAACAAGAAGCCTGTGCTGATCCCGATCGCCGGAGAGGGAGCCAGCCAGA
TGGAAATTGAGCGGGAGACTCATTTCGATGGGACTAACTACCTGGCCATCAGACCG
GGCGTGGTGATTGGATATAGCAGGAACGAAAAGACTAATGCAGCGTTGGAAGCGGC
AGGAATCAAGGTCCTGCCGTTCCACGGAAATCAGCTTTCGCTCGGTATGGGGAACGC
GAGATGTATGTCGATGCCGCTGTCCCGCAAGGACGTGAAGTGG (SEQ ID NO: 2)

Name: Arginine deiminase_OptHs

Sequence:
AAGCTGACCGGTGCCGCCACCATGTCGGTGTTTGA
TTCAAAGTTCAAAGGAATCCACGTGTACTCAGAAA
TTGGCGAGCTCGAAAGCGTGCTGGTGCACGAACCC
GGAAGAGAGATCGACTATATCACTCCAGCGCGCCT
GGATGAACTGCTGTTCTCGGCCATCTTGGAATCGC
ATGACGCACGCAAGGAACACAAGCAATTTGTCGCC
GAACTTAAAGCCAATGACATCAATGTGGTCGAACT
GATTGACCTGGTCGCGGAAACCTACGATCTGGCGA
GCCAGGAAGCCAAAGATAAGCTCATCGAGGAGTTT
TTGGAGGACAGCGAACCAGTGCTCTCCGAAGAACA
TAAGGTCGTGGTGAGGAATTTCCTCAAAGCTAAAA
AGACTTCCCGGAAGCTGGTGGAGATTATGATGGCT
GGCATCACCAAATACGATCTTGGCATCGAGGCCGA
CCACGAGCTGATCGTCGATCCTATGCCGAATCTGT
ACTTTACCCGCGACCCCTTCGCCTCGGTCGGAAAT
GGGGTGACTATCCACTACATGCGCTACAAAGTCAG
ACAACGGGAAACCCTCTTCTCCCGGTTCGTGTTCT
CCAACCATCCGAAGCTGATCAACACCCCTTGGTAC
TACGACCCATCACTGAAGCTCTCCATCGAAGGCGG
TGACGTGTTCATCTACAACAATGATACCCTCGTGG
TGGGCGTGTCAGAGCGGACCGACTTGCAAACTGTG
ACCCTTCTGGCTAAGAACATCGTGGCAAACAAAGA
GTGCGAGTTCAAGCGCATCGTCGCTATCAACGTCC
CGAAGTGGACGAACCTCATGCACCTTGACACCTGG
CTGACGATGTTGGACAAAGACAAGTTCCTCTACTC
CCCGATTGCAAACGATGTGTTCAAGTTTTGGGATT
ACGACTTGGTGAACGGAGGAGCCGAGCCACAGCCA
GTGGAGAACGGACTGCCCCTCGAAGGACTGCTGCA
GAGCATCATCAACAAGAAGCCTGTGCTGATCCCGA
TCGCCGGAGAGGGAGCCAGCCAGATGGAAATTGAG
CGGGAGACTCATTTCGATGGGACTAACTACCTGGC

FIG. 14 (contd.)

CATCAGACCGGGCGTGGTGATTGGATATAGCAGGA
ACGAAAAGACTAATGCAGCGTTGGAAGCGGCAGGA
ATCAAGGTCCTGCCGTTCCACGGAAATCAGCTTTC
GCTCGGTATGGGGAACGCGAGATGTATGTCGATGC
CGCTGTCCCGCAAGGACGTGAAGTGGATGGCCTCA
TCCTACCCTTACGATGTCCCGGACTACGCTATG
GCTAGC (SEQ ID NO: 3)

Legend:
Non Coding regions
Coding region for ADI
Hemagglutinin tag

| | |
|---|---|
| Sequence Type: | DNA |
| Sequence Details: | Size: 1302bp |
| | GC:54% |
| | A=339 T=268 G=352 C=343 |
| InhouseVectorSequence: | AAGCTG ACCGGT GCCGCCACC (SEQ ID NO: 4) |

Translate
MSVFDSKFKGIHVYSEIGELESVLVHEPGREIDYITPARLDELLFSAILESHD
ARKEHKQFVAELKANDINVVELIDLVAETYDLASQEAKDKLIEEFLEDSEPVLSEEHKVV
VRNFLKAKKTSRKLVEIMMAGITKYDLGIEADHELIVDPMPNLYFTRDPFASVGNGVTIH
YMRYKVRQRETLFSRFVFSNHPKLINTPWYYDPSLKLSIEGGDVFIYNNDTLVVGVSER
TDLQTVTLLAKNIVANKECEFKRIVAINVPKWTNLMHLDTWLTMLDKDKFLYSPIANDVF
KFWDYDLVNGGAEPQPVENGLPLEGLLQSIINKKPVLIPIAGEGASQMEIERETHFDGT
NYLAIRPGVVIGYSRNEKTNAALEAAGIKVLPFHGNQLSLGMGNARCMSMPLSRKDVK
WMASSYPYDVPDYAM*(SEQ ID NO: 5)

US 10,435,682 B2

ARGININE DEIMINASE GENE THERAPY FOR DISORDERED PROTEINS

CROSS-REFERENCE TO RELATED APPLICATIONS

This nonprovisional application claims priority to U.S. Provisional Patent Application Ser. No. 62/297,488, the entirety of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,815 bytes ASCII (Text) file named "210112-9016-US02 ST25.txt," created on Feb. 21, 2017.

TECHNICAL FIELD

The disclosure relates to methods of decreasing aggregation of disordered protein in a subject.

BACKGROUND

Aggregation of disordered protein has been implicated in a wide variety of diseases. Diseases characterized by aggregation of disordered protein include neurodegenerative diseases such as tauopathies and synucleinopathies. Currently, no effective treatments exist for most neurodegenerative diseases, highlighting the need for continued developments in the field.

SUMMARY

The present invention is directed to a composition comprising arginine deiminase. The arginine deiminase composition may comprise a vector comprising a nucleotide sequence encoding an arginine deiminase. The arginine deiminase composition may be used in a method of reducing aggregation of disordered protein in a subject. The arginine deiminase composition may be used in a method of treating a disease characterized by aggregation of disordered protein in a subject. The subject may be human. The disordered protein may be tau. The disordered protein may be alpha-synuclein. The arginine deiminase composition may reduce aggregation of disordered protein without producing toxic levels of polyamines in the subject.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 2A-D show expression of viral constructs in injected mice. FIGS. 2A-B show anti-HA staining in AAV9-GFP and AAV9-ADI injected mice. FIGS. 2C-D show anti-GFP staining in AAV9-GFP and AAV9-ADI injected mice.

FIGS. 4A-I show reduction of tau levels in Tg4510 mice injected with AAV9-ADI.

FIGS. 4A, 4C, and 4E show baseline levels of total tau in the anterior cortex (ACX), hippocampus (HPC), and entorhinal cortex and amygdala (ECX) of Tg4510 mice injected with AAV9-GFP. FIGS. 4B, 4D, and 4F show reduction of tau levels in the ACX, HPC and ECX in Tg4510 mice injected with AAV9-ADI. Quantification of total tau is shown in FIG. 4G. Quantification of phosphorylated tau is shown in FIGS. 4H-I. Statistical analysis was performed using 1-way ANOVA with multiple comparisons and Fisher's LSD. n=7-9/group.

FIGS. 5A-G show reduction of neurofibrillary tangles (NFT) in Tg4510 mice injected with AAV9-ADI. FIGS. 5A, 5C, and 5E show baseline levels of NFT as measured by Gallyas silver in the ACX, HPC, and ECX of Tg4510 mice injected with AAV9-GFP.

FIGS. 5B, 5D, and 5F show reduction of NTF in the ACX, HPC, and ECX in Tg4510 mice injected with AAV9-ADI. Results are quantified in FIG. 5G. Statistical analysis was performed using 1-way ANOVA with multiple comparisons and Fisher's LSD. n=7-9/group.

FIGS. 6A-D show reduction of hippocampal atrophy following ADI injection. FIG. 6A depicts normal hippocampal volume in a non-transgenic mouse injected with AAV9-GFP. FIG. 6B shows levels of atrophy in Tg4510 mice injected with AAV9-GFP. FIG. 6C shows levels of atrophy in Tg4510 mice injected with AAV9-ADI. AAV9-ADI injected mice show reduced levels of atrophy as compared to AAV9-GFP injected mice. Results are quantified in FIG. 6D. Statistical analysis was performed using 1-way ANOVA with multiple comparisons and Fisher's LSD. n=7-9/group.

FIGS. 7A-D show that ADI increases autophagy in Tg4510 mice. FIG. 7A shows endogenous levels of p62 in the HPC of non-transgenic mice injected with AAV9-GFP. FIG. 7B depicts levels of p62 in in the HPC of Tg4510 mice injected with AAV9-GFP. FIG. 7C shows that p62 is significantly decreased in Tg4510 mice given AAV9-ADI, as compared to mice given AAV9-GFP, indicating increased autophagy following ADI injection. FIG. 7D depicts quantification of p62 as a measure of % area in both the ACX and HPC. Statistical analysis was performed using 1-way ANOVA with multiple comparisons and Fisher's LSD. n=7-9/group.

FIG. 11 shows the nucleotide sequence of bacterial arginine deiminase (SEQ ID NO: 1).

FIG. 12 shows the nucleotide sequence of a mammalianized arginine deiminase (SEQ ID NO: 2).

FIG. 13 shows a sequence alignment comparing the sequence of bacterial arginine deiminase (SEQ ID NO: 1) to that of a mammalianized ADI (SEQ ID NO: 2).

FIG. 14 shows the nucleotide sequence of the mammalianized ADI fused to an HA tag (SEQ ID NO: 3). The first 21 nucleotides of SEQ ID NO: 3 correspond to SEQ ID NO: 4 ("InHouseVectorSequence"). The translated sequence for the resulting construct is shown in SEQ ID NO: 5.

DETAILED DESCRIPTION

Figure 1:
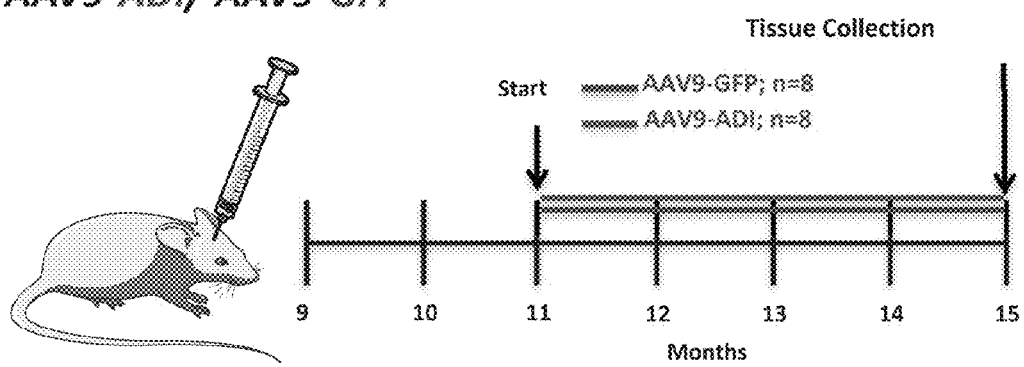
FIG. 1 depicts the experimental design of a study that shows the effects of ADI overexpression on tau pathology in Tg4510 mice. Tg4510 mice were injected with AAV9-ADI or AAV9-GFP at 11 months of age. Viral expression of the transgene was allowed for 4 months. Mice were sacrificed at 15 months of age, and tissues were collected for analysis.

Arginine is one of the most versatile amino acids in animal cells, serving as a precursor for the synthesis not only of proteins but also of nitric oxide, urea, polyamines, proline, glutamate, creatine and agmatine. Polyamines have been shown to modify disordered proteins such as tau, amyloid beta, and alpha synuclein. However, the formation and aggregation of polyamines can be potentially toxic to cells. As such, the proper balance of polyamines is essential for cell viability.

The present invention relates to the discovery that arginine deiminase reduces aggregation of proteins without producing toxic levels of polyamines. Disclosed herein are compositions comprising arginine deiminase and the use of such compositions in a method for reducing aggregation of disordered protein in a subject.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

The term "administration" or "administering" is used throughout the specification to describe the process by which the disclosed compositions may be delivered to a subject.

Administration will often depend upon the amount of composition administered, the number of doses, and duration of treatment. Multiple doses of the composition may be administered. The frequency of administration of the composition can vary depending on any of a variety of factors, such as level of protein aggregation or neurodegeneration, and the like. The duration of administration of the composition, e.g., the period of time over which the composition is administered, can vary, depending on any of a variety of factors, including patient response, etc.

The amount of the composition administered can vary according to factors such as the degree of susceptibility of the individual, the age, sex, and weight of the individual, idiosyncratic responses of the individual, the dosimetry, and the like. Detectably effective amounts of the composition of the present disclosure can also vary according to instrument and film-related factors. Optimization of such factors is well within the level of skill in the art.

"Arginine deiminase", or "ADI" as used interchangeable herein, refers to an enzyme that catalyzes the conversion of L-arginine and water into citrulline and ammonia.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof.

"Disordered protein" as used herein refers to proteins or regions of proteins that lack a fixed or ordered tertiary structure. Disordered proteins include intrinsically disordered proteins (IDPs) and intrinsically unstructured proteins (IUPs). Such proteins may be fully disordered or partially disordered and generally lack the stability of proteins with fixed or ordered tertiary structures. Disordered proteins may be prone to aggregation. Examples of disordered proteins prone to aggregation include tau and α-synuclein.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "genome" as used herein includes an organism's chromosomal/nuclear genome as well as any mitochondrial, and/or plasmid genome.

The term "heterologous" as used herein refers to a nucleic acid or protein comprising two or more subsequences that are not found in the same relationship to each other in nature. For instance, a heterologous protein indicates that the protein comprises two or more subsequences that are not found in the same relationship to each other in nature (e.g., a "fusion protein," where the two subsequences are encoded by a single nucleic acid sequence).

"Mammalianized" as used herein refers to the process optimizing expression of a protein in a mammalian system. Proteins may be mammalianized through codon usage. Codon usage refers to the selection of codons that are optimized for translation on mammalian ribosomes and subsequent expression in a mammalian system. A mammalian system may include mammalian cells, such as HeLa cells, an animal model, or a human.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. A motif may include 3, 4, 5, 6, or 7 sequential amino acids.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods. The terms "polynucleotide," "nucleotide sequence" "nucleic acid," "nucleic acid molecule," and "oligonucleotide" are also used interchangeably herein to refer to a heteropolymer of nucleotides.

"Promoter" as used herein means a synthetic or naturally-derived molecule which is capable of conferring, activating or enhancing expression of a polynucleotide in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant vectors express genes that are not found within the native (naturally occurring) form of the vector or express a second copy of a native gene that is otherwise normally or abnormally expressed, under expressed or not expressed at all.

"Sample" or "test sample" as used herein can mean any sample in which the presence and/or level of a target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. The sample may comprise an aliquot. The sample may comprise a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). The subject may be a human or a non-human. The subject or patient may be undergoing other forms of treatment.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Synucleinopathy" as used herein refers to a class of neurodegenerative diseases associated with the pathological aggregation of α-synuclein protein.

"Tauopathy" as used herein refers to a class of neurodegenerative diseases associated with the pathological aggregation of tau protein.

A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the composition may be given as a preventative treatment or therapeutically at any stage of disease progression, before or after symptoms, and the like), applications or dosages and is not intended to be limited to a particular formulation, combination or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art.

"Treatment" or "treating" as used herein, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

As used herein, the term "toxic" refers to an amount of a chemical entity or substance (e.g., polyamines) that would be harmful the subject. "Cytotoxic" refers to a chemical entity or substance that is toxic to cells.

The terms "transformation," "transfection," and "transduction" as used interchangeably herein refer to the introduction of a heterologous nucleic acid into a cell. Such introduction into a cell may be stable or transient. Thus, in some embodiments, a host cell or host organism is stably transformed with a polynucleotide of the invention. In other embodiments, a host cell or host organism is transiently transformed with a polynucleotide of the invention. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid. In some embodiments, the nucleotide sequences can be expressed transiently and/or they can be stably incorporated into the genome of the host organism.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" is used herein to describe a peptide or polypeptide that differs in amino acid sequence by the insertion, deletion, or conservative substitution of amino acids, but retain at least one biological activity. Variant is also used herein to describe a protein with an amino acid sequence that is substantially identical to a referenced protein with an amino acid sequence that retains at least one biological activity. Representative examples of "biological activity" include the ability to metabolize arginine.

Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid.

2. Arginine Deiminase Composition

The invention discloses compositions comprising an arginine deiminase. The compositions may comprise the arginine deiminase encoded by the nucleotide sequence of SEQ ID NO: 1 or a variant thereof. The disclosed compositions may comprise a recombinant arginine deiminase. The disclosed compositions may comprise a mammalianized arginine deiminase. For example, the disclosed compositions may comprise the mammalianized arginine deiminase encoded by the nucleotide sequence of SEQ ID NO: 2 or a variant thereof.

The arginine deiminase composition may comprise an arginine deiminase in a vector delivery system. For example, the arginine deiminase composition may comprise a vector comprising a nucleotide sequence encoding an arginine deiminase. The nucleotide sequence may be codon optimized for expression in a specific cell type. For example, the nucleotide sequence may be mammalianized. The arginine deiminase composition may comprise a vector comprising the nucleotide sequence of SEQ ID NO: 1 or a variant thereof. The arginine deiminase composition may comprise a vector comprising the nucleotide sequence of SEQ ID NO: 2 or a variant thereof. The vector may further comprise initiation and termination signals operably linked to regulatory elements including a promoter. The vector may further include a polyadenylation signal capable of directing expression in the cells of an individual or mammal to which the arginine deiminase composition is administered. The vector may further comprise a reporter gene, such as GFP. The vector may further comprise a selectable marker.

The vector delivery system may be any vector delivery system. The vector may be a viral vector. Any viral vector or hybrid thereof may be used.

The viral vector may be an adenoviral vector. The vector may be an adeno-associated virus (AAV) vector. The AAV vector is a small virus belonging to the genus Dependovirus of the Parvoviridae family that infects humans and other primate species. AAV may be an attractive vector system for use according to the present invention as it has a high frequency of integration and it can infect nondividing cells, thus making it useful for delivery of genes into mammalian cells, for example, in tissue culture or in vivo. AAV has a broad host range for infectivity.

The AAV vector may be a modified AAV vector. The modified AAV vector may have enhanced tissue tropism. The modified AAV vector may be capable of delivering and expressing arginine deiminase in the cell of a mammal. The modified AAV vector may be based on one or more of several capsid types, including AAV1, AAV2, AAV5, AAV6, AAV8, and AAV9.

The vector may be a retroviral vector. Retroviruses have promise as gene delivery vectors due to their ability to integrate their genes into the host genome, transferring a large amount of foreign genetic material, infecting a broad spectrum of species and cell types and of being packaged in special cell-lines.

The vector may be a lentiviral vector. Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe.

The vector may be a recombinant lentiviral vector. Recombinant lentiviral vectors are capable of infecting non-dividing cells and can be used for both in vivo and ex vivo gene transfer. One may target the recombinant virus by linkage of the envelope protein with an antibody or a particular ligand for targeting to a receptor of a particular cell-type. By inserting a sequence (including a regulatory region) of interest into the viral vector, along with another gene that encodes the ligand for a receptor on a specific target cell, the vector is now target-specific.

Other viral vectors may be employed as constructs in the arginine deiminase composition. Vectors derived from viruses such as vaccinia virus, Epstein-Barr virus, sindbis virus, cytomegalovirus and herpes simplex virus may be employed.

The arginine deiminase composition may be an injectable preparation. Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful. The arginine deiminase composition may further comprise a pharmaceutically acceptable excipient.

3. Methods of Reducing Aggregation of Disordered Protein

The invention discloses a method for reducing aggregation of a disordered protein in a subject. The method may comprise administering the arginine deiminase composition to the subject. Disordered protein refers to proteins or regions of proteins that lack a fixed or ordered tertiary structure. Disordered proteins include intrinsically disordered proteins and intrinsically unstructured proteins. Such proteins are generally prone to aggregation and may be associated with neurodegenerative disease.

The disordered protein may be tau. Tau may exist in multiple forms, including insoluble, monomeric, and high molecular weight multimers. Aggregation of tau may be indicated by the presence of neurofibrillary tangles. Neurofibrillary tangles may form in the central nervous system of a subject. For example, neurofibrillary tangles may form in entorhinal cortex or the hippocampus of the subject. Reducing aggregation of tau may reduce of the amount of neurofibrillary tangles in the affected tissue. The primary component of neurofibrillary tangles is hyperphosphorylated tau. Reducing aggregation of tau may include reducing levels of any one or more of total tau, phosphorylated tau, or hyperphosphorylated tau in the subject.

The disordered protein may be alpha-synuclein. Multiple forms of alpha synuclein may be reduced, including insoluble, monomeric, and high molecular weight multimers. Alpha-synuclein is the primary component of Lewy bodies. Reducing aggregation of alpha-synuclein may reduce the amount of Lewy bodies in the affected tissue. For example, reducing aggregation of alpha-synuclein may reduce the amount of Lewy bodies in the hippocampus. Reducing aggregation of alpha-synuclein may reduce the amount of Lewy bodies in the entorhinal cortex.

The disordered protein may be post-translationally modified. For example, the disordered protein may be modified by phosphorylation, oxidation, nitrosylation, glycation, or glycosylation. Reducing aggregation of disordered protein may reduce the amount of any form of the post-translationally modified disordered protein in the subject. For example, reducing aggregation of the disordered protein may reduce the levels of phosphorylated disordered protein in the subject. For example, reducing aggregation of disordered tau could reduce levels of phosphorylated tau in the subject.

The method may comprise administering to the subject the arginine deiminase composition. The arginine deiminase composition may decrease aggregation of a disordered protein without producing toxic levels of polyamines in the subject. Levels of polyamines, or their metabolites may be measured before, during or after administration of the composition to monitor levels in the subject.

Indicators of toxicity are known in the art. For example, toxicity may cause damage to DNA, RNA, lipids, proteins, and various cellular compartments. Sub lethal doses of cytotoxic compositions may result in decreased cell proliferation. Lethal doxes of toxic compositions may result in loss of membrane integrity and cell death. Cytotoxicity may be measured by standard cytotoxicity assays, such as assays that measure cell viability and cell death. Examples of standard cytotoxicity assays include MTT assays, ATP assays, Neutral Red uptake assays, ELISA, MTS assays, SRB assays, WST assays, and clonogenic assays. Toxicity may also be determined by measuring cell death, such as by apoptosis or necrosis.

The subject may be any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). The subject may be a human. The subject may be a non-human.

The subject may be diagnosed with a disease characterized by aggregation of disordered protein. The disease characterized by aggregation of disordered protein may be a tauopathy. The tauopathy may be Alzheimer's disease, Huntington's disease, Pick's disease, primary age-related tauopathy, chronic traumatic encephalopathy, dementia pugilistica, progressive supranuclear palsy, corticobasal degeneration, frontotemporal dementia, parkinsonism linked to chromosome 17, Lytico-Bodig disease, ganglioglioma, gangliocytoma, meningioangiomatosis, tangle predominant dementia, postencephalitic parkinsonism, subacute scelrosing panencephalitis, lead encephalopathy, tuberous sclerosis, Hallervorden-Spatz disease, lipofuscinosis, argyrophilic grain disease, or frontotemporal lobar degeneration.

The disease characterized by aggregation of disordered protein may be a synucleinopathy. The synucleinopathy may be Parkinson's disease, dementia with Lewy bodies, or multiple system atrophy, for example.

The arginine deiminase composition may be administered to the subject by several different means. For instance, the arginine deiminase composition may generally be administered parenterally, intraperitoneally, intravascularly, or intrapulmonarily. The arginine deiminase composition may be administered to the subject in dosage unit formulations containing conventional nontoxic pharmaceutically acceptable carriers, adjuvants, and vehicles as desired. The arginine deiminase composition may be administered parenterally.

The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Delivery methods are preferably those that are effective to circumvent the blood-brain barrier and are effective to deliver compositions to the central nervous system. For example, delivery methods may include the use of nanoparticles. Positively charged lipids are particularly preferred for such nanoparticles, and may include liposomes, niosomes, micelles, multilamellar vesicles, unilamellar vesicles, and polymersomes. The particles may be of any suitable structure so long as the arginine deiminase is contained therein. The preparation of such lipid particles is well known in the art. See, e.g., U.S. Pat. No. 4,880,635 to Janoff et al.; U.S. Pat. No. 4,906,477 to Kurono et al.: U.S. Pat. No. 4,911,928 to Wallach; U.S. Pat. No. 4,917,951 to Wallach; U.S. Pat. No. 4,920,016 to Allen et al.: U.S. Pat. No. 4,921,757 to Wheatley et al.; etc.

The arginine deiminase composition may be administered in a bolus directly into the central nervous system. The arginine deiminase composition may be administered to the subject in a bolus once, or multiple times. When administered multiple times, the arginine deiminase composition may be administered at regular intervals or at intervals that may vary during the treatment of a subject.

The arginine deiminase composition may be administered by continuous infusion into the central nervous system. Non-limiting examples of methods that may be used to deliver the compositions provided herein into the central nervous system by continuous infusion may include pumps, wafers, gels, foams and fibrin clots. The arginine deiminase composition may be delivered into the central nervous system by continuous infusion using an osmotic pump. An osmotic mini pump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space. The arginine deiminase composition may be delivered into the central nervous system by continuous infusion using a pump.

The arginine deiminase composition may be delivered into the central nervous system by intrathecal administration. A catheter may be placed in the intrathecal lumbar space of the subject. The proximal end of the catheter may be attached to a dosing pedestal that may extend through the skin. The arginine deiminase composition may be administered as a bolus injection. The arginine deiminase composition may be administered as a continuous infusion.

The arginine deiminase composition may be delivered to the subject in any dose sufficient to achieve the desired therapeutic effect. For example, a therapeutically effective amount of a compound of the disclosed arginine deiminase composition may be about 1 mg arginine deiminase/kg body weight to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

4. Kits

The invention further discloses a kit, which may be used to reduce aggregation of disordered protein in a subject. The kit comprises at least the arginine deiminase composition. Also provided herein is a kit which may be used in a method of treating a disease characterized by aggregation of disordered protein in a subject.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

5. Examples

The foregoing may be better understood by reference to the following examples, which are presented for purposes of illustration and are not intended to limit the scope of the invention. The present invention has multiple aspects, illustrated by the following non-limiting examples.

Example 1—Cloning and Expression of Recombinant AAV Constructs

Figure 13:
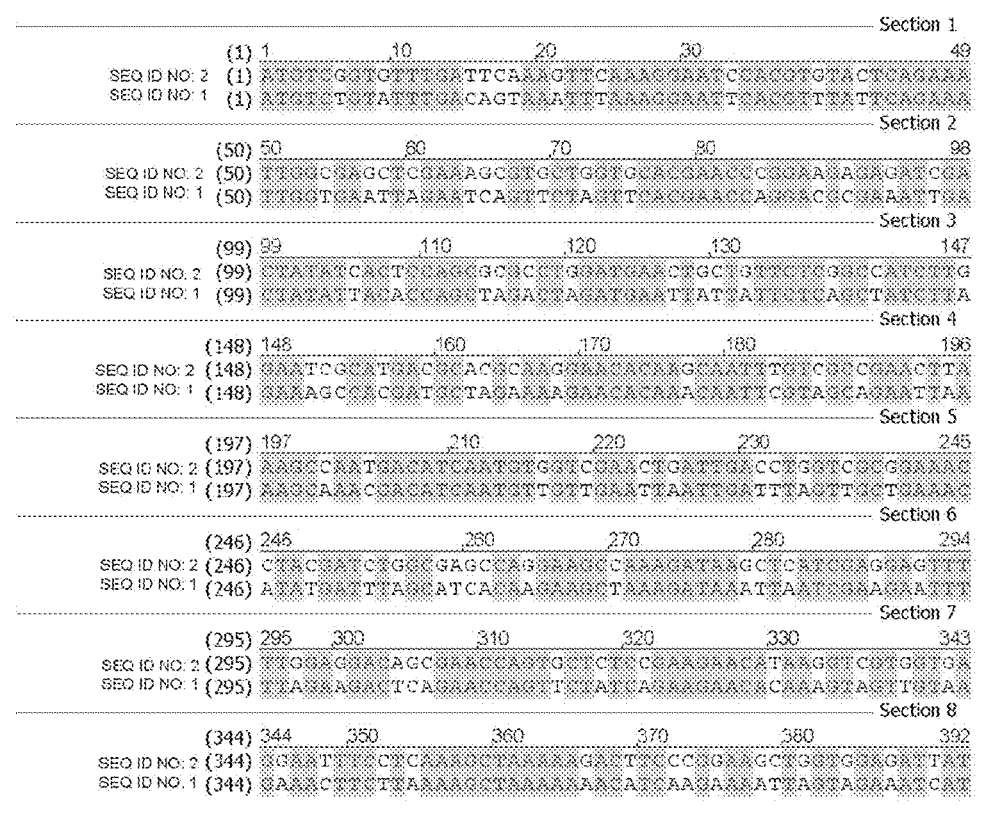
Figure 13:
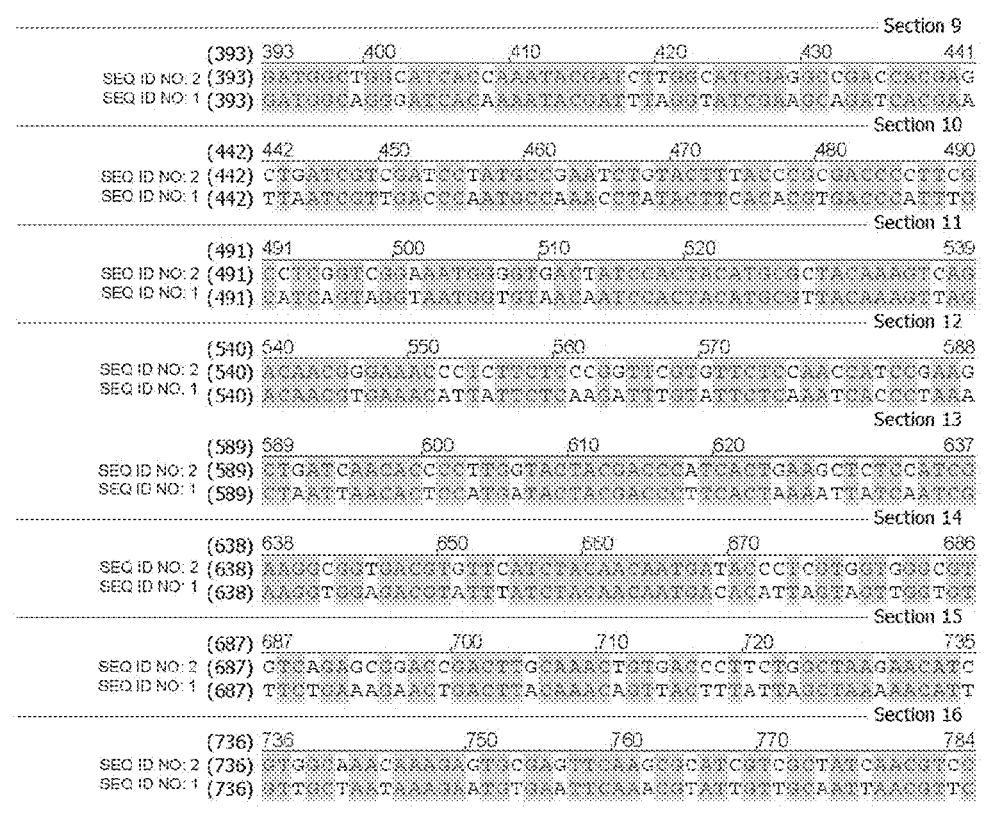
Figure 13:
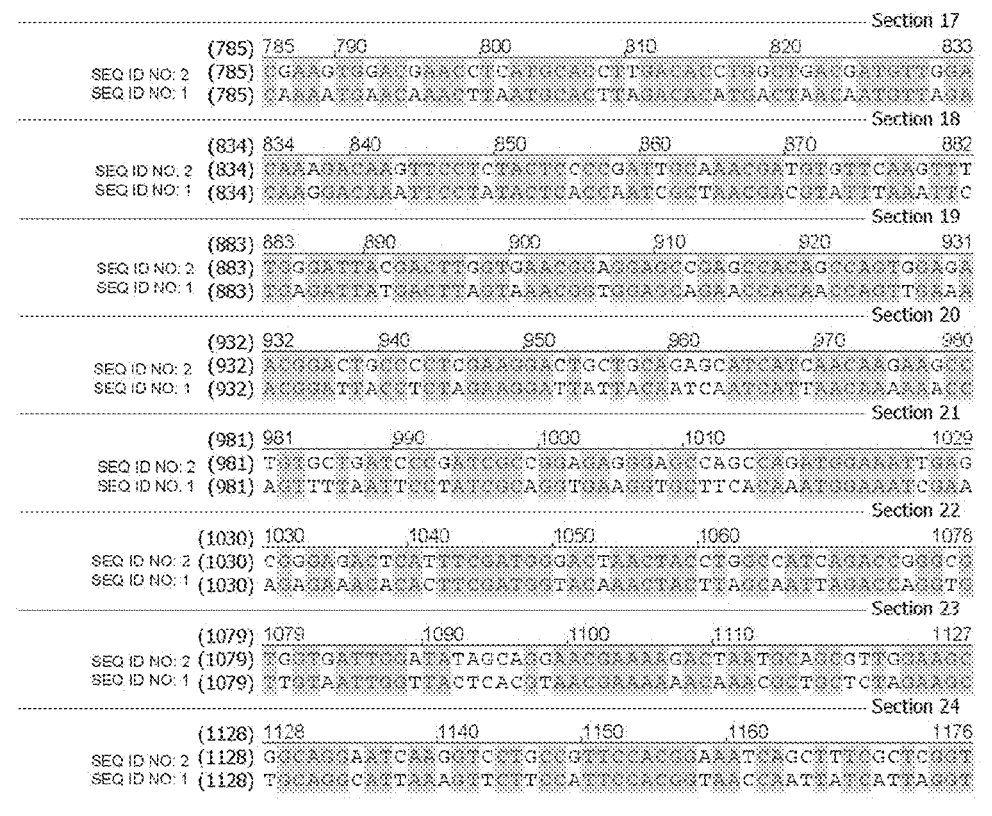
Figure 13:
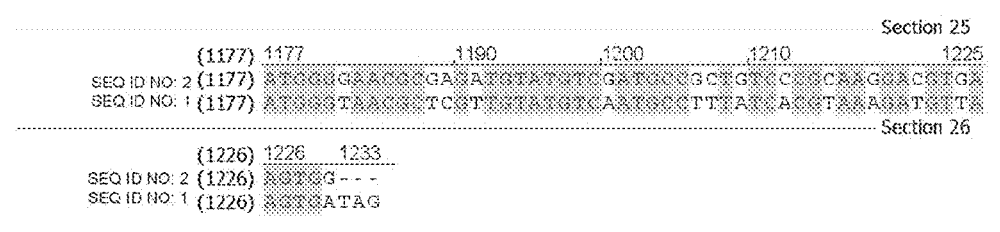

ADI enzyme is widely expressed in bacteria and uses the substrates L-arginine and water to generate L-citrulline and ammonia. The sequence of bacterial ADI is provided in SEQ ID NO:1. The bacterial gene ADI (E.C. 3.5.3.6) was mammalianized through codon usage and fused to a hemagglutinin tag (HA tag). The sequence of mammalianized ADI is provided in SEQ ID NO: 2. A sequence alignment comparing the sequence of mammalianized ADI to that of the bacterial arginine deiminase is shown in FIG. 13. Yellow highlighted text indicates codons that are unsubstituted in the mammalianized ADI compared to the bacterial sequence.

Figure 10:
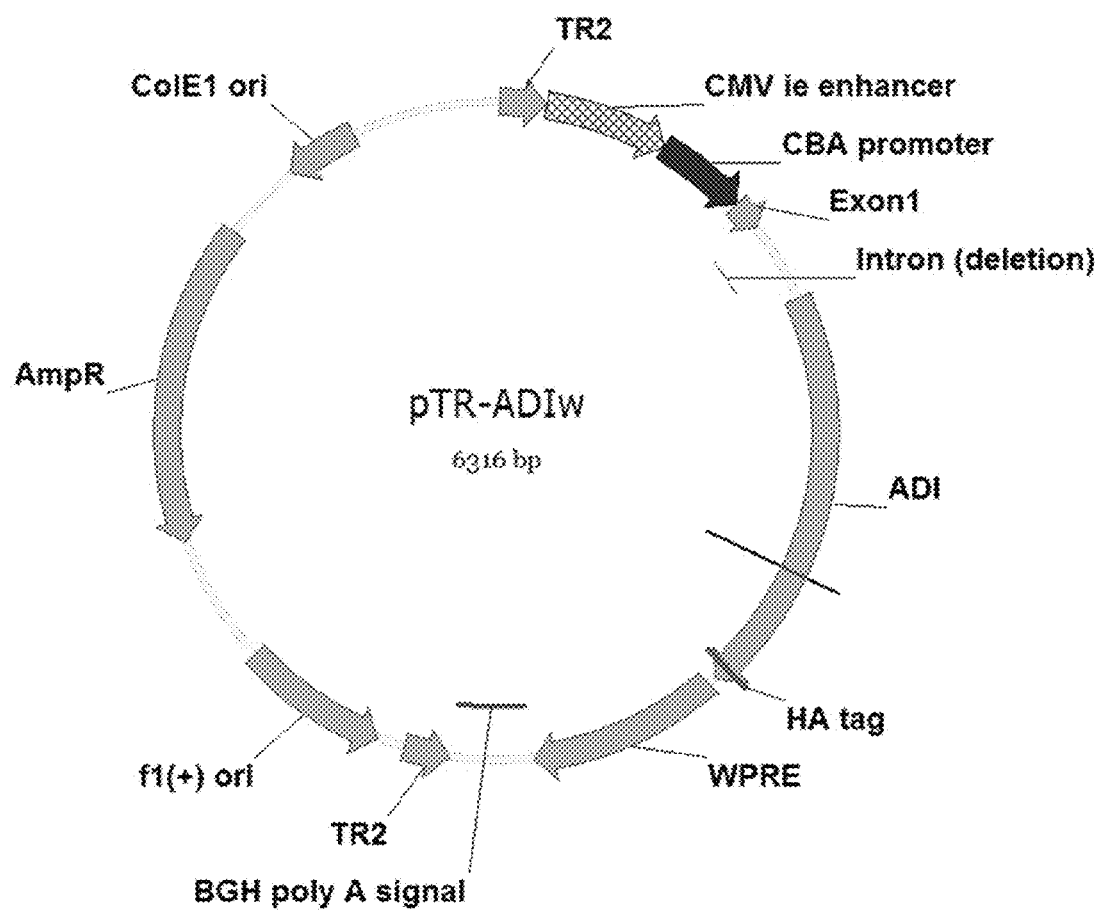
FIG. 10 shows the vector used for AAV9-ADI and AAV9-GFP.

The mammalianized ADI and GFP were expressed in AAV9 using the vector pTR-ADIw, shown in FIG. 10, and methods known in the art to produce viral particles. The resulting constructs are herein referred to as AAV9-ADI and AAV9-GFP, respectively.

HeLa cells were transfected with AAV9-ADI or AAV9-EC to confirm mammalian expression of the viral construct. Following transient transfection, cells were harvested and protein expression was analyzed by Western blot using a rat anti-HA antibody (Clone 3F10 from Sigma Aldrich Cat#12158167001). As shown in FIG. 2A, successful expression of AAV9-ADI in a mammalian system was confirmed by a strong band at the appropriate size of the HA tag (46 kDa).

Example 2—ADI Overexpression Reduces Tau Neuropathology

Mouse Model:
The ability of ADI to reduce aggregation of proteins was tested in a mouse model of tauopathy. The Tg4510 mouse is a versatile tauopathy model that provides temporal and spatial control over mutant tau transgene expression. The mice express a repressible form of human tau containing the P301L mutation that has been linked with familial frontotemporal dementia. The transgene is downstream of a tetracycline operon-responsive element (TRE), and expression is driven by a second transgene containing a tetracycline-controlled transactivator (tTA) under control of a promoter such as CaMKII-α. Tau is constitutively expressed until inactivated by administration of the tetracycline analog doxycycline (dox).

Figure 3A:
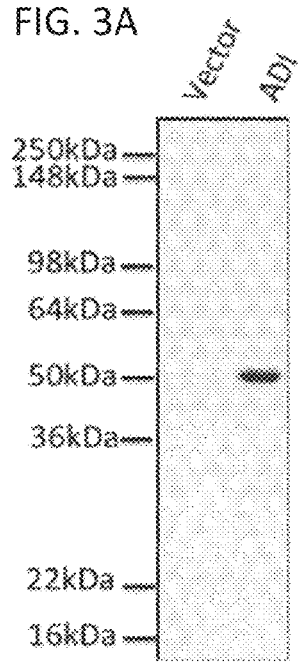
FIGS. 3A-B depict arginine deiminase (ADI) 48.5 kDA expression in the mouse CNS.
Figure 3B:
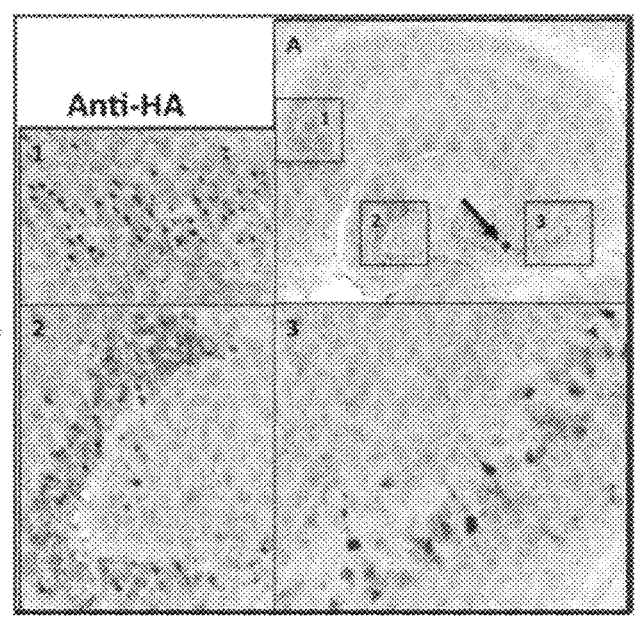
Figure 8A:
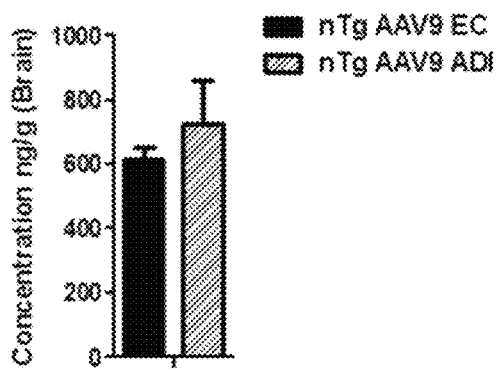
FIGS. 8A-D show that overexpression of ADI does not increase levels of polyamines (putrescine, spermidine, spermine, ornithine) in the CNS.
Figure 8B:
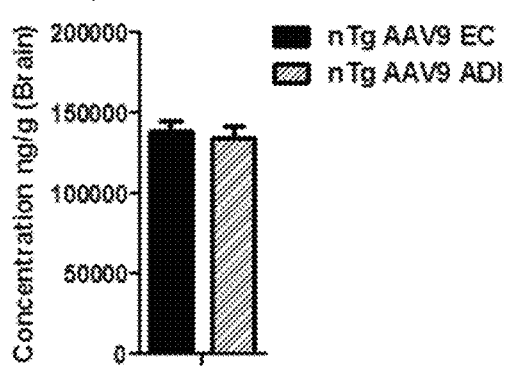
Figure 8C:
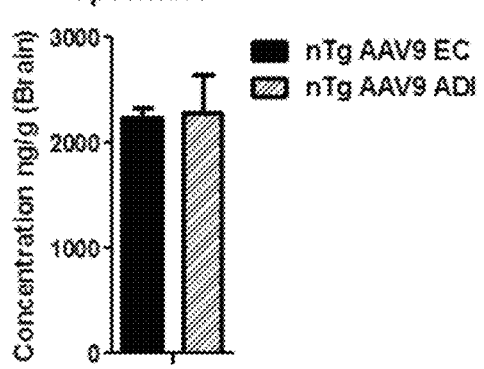
Figure 8D:
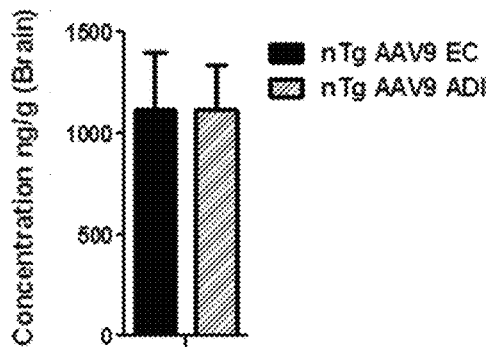
Figure 8E:
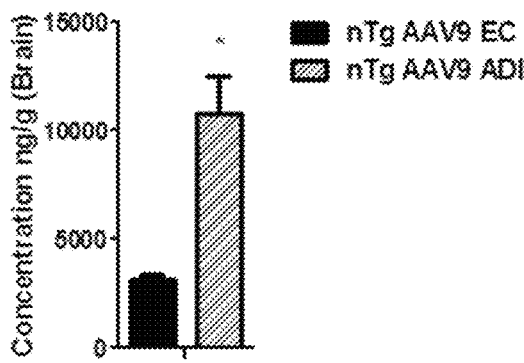
FIG. 8E shows that overexpression of ADI increases levels of citrulline, confirming functional activity of the enzyme. Statistical analysis was performed using unpaired student t-test. n=6-8/group.

Experimental Design:
The recombinant AAV constructs AAV9-ADI or AAV9-GFP were injected into the bilateral anterior cortex (ACX) or hippocampus (HPC) of 11 month old Tg4510 mice. Sterotaxic coordinates used were HPC (AP: −2.7; LAT: +/−2.7; DV: −3.0) and CTX (AP: +1.7; LAT: +/−2.2; DV: −3.0). Viral titers were 2.4e12 vg/ml for AAV9-ADI, and 2.0e12 vg/ml for AAV9-GFP. Virus was injected at a rate of 1.5 ul/minute using convection enhanced delivery of the virus for a total volume of 2.5 μl/site. Expression of the transgene was allowed for 4 months. Mice were sacrificed at 15 months of age, and expression of the transgene was confirmed by immunohistochemistry. As shown in FIG. 2, positive staining for HA was seen in tissue injected with AAV9-ADI (FIG. 2B), indicating increased expression of ADI relative to AAV9-GFP injected controls (FIG. 2A). Positive staining for GFP was seen in tissue injected with AAV9-GFP (FIG. 2C), but not AAV9-ADI (FIG. 2D). As shown in FIG. 3B, ADI expression was confirmed by anti-HA staining in multiple hippocampal areas, including CA3, the dentate gyrus, and the subiculum.

Tau Expression:
As shown in FIG. 4, mice injected with AAV9-ADI display reduced levels of total tau the ACX, HPC and ECX in comparison to mice injected with AAV9-GFP. These results demonstrate that overexpression of ADI reduces tau levels in Tg4510 mice. Phosphorylation of tau may promote aggregation of the protein. Hyperphosphorylation of tau can result in the self-assembly of tangles of paired helical filaments and straight filaments, which are involved in the pathogenesis of tauopathies such as Alzheimer's disease and frontotemporal dementia. Mice injected with AAV9-ADI also display reduced levels of phosphorylated tau in the ACX, HPC, and ECX in comparison to mice injected with AAV9-GFP. These results indicate that overexpression of ADI reduces levels of total tau and phosphorylated tau in the CNS.

NFT:
Neurofibrillary tangles are aggregates of hyperphosphorylated tau protein. As shown above, ADI overexpression reduces the levels of total tau and phosphorylated tau in the mouse brain. To assess the hypothesis that ADI also promotes reduction of NFT, gallyas silver staining was conducted. As shown in FIG. 5, mice injected with AAV9-ADI display reduced neurofibrillary tangles in the ACX, HPC, and ECX in comparison to mice injected with AAV9-GFP.

Hippocampal Atrophy:
Atrophy of the hippocampus is another characteristic associated with multiple tauopathies, including Alzheimer's disease. Non-transgenic mice and Tg4510 mice were injected with AAV9-GFP and baseline measurements of hippocampal volume were obtained. As shown in FIG. 6, hippocampal volume of Tg4510 mice was significantly smaller than that of non-transgenic controls. However, injection of AAV9-ADI significantly increased hippocampal volume in Tg4510 animals. This data indicates that overexpression of ADI prevents hippocampal atrophy in Tg4510 mice.

Autophagy:
Autophagy of proteins is an essential process for eliminating misfolded proteins and preventing aggregation. To assess the effect of ADI expression on autophagy, levels of the autophagy marker p62 were measured. Non-transgenic mice and Tg4510 mice were injected with AAV9-GFP and baseline measurements of p62 were obtained. As shown in FIG. 8, endogenous levels of p62 are significantly higher in the hippocampus of Tg4510 mice compared to non-transgenic controls, indicating impaired autophagy. Injection of AAV9-ADI into the hippocampus of Tg4510 mice significantly reduced p62 expression, indicating partial rescue of autophagy in these animals. This data suggests that overexpression of ADI increases autophagy, which may help promote clearance of aggregated proteins from the brain.

Polyamine Levels:

Levels of the polyamines putrescine, spermidine, spermine, ornithine, and citrulline were quantified in the CNS 4 months after injection with AAV9-ADI or AAV9-GFP. As shown in FIGS. 8A-D, levels of polyamines were not significantly increased in animals injected with AAV9-ADI in comparison to AAV9-EC injected controls. To ensure enzymatic activity of ADI, levels of citrulline were measured. Animals injected with AAV9-ADI show significantly higher levels of citrulline compared to AAV9-EC injected animals, indicating that mammalianized ADI retained functional enzymatic activity.

Example 3—ADI Overexpression Reduces α-Synuclein Neuropathology

Mouse Model: The ability of ADI to reduce aggregation of proteins in synucleinopathies was tested in a mouse model of Lewy Body Dementia. Mice hemizygous for the human alpha synuclein mutant (A53T) transgene (mutant SNCA*A53T) were used. The expression of SNCA*A53T is turned on by the tetracycline-operating promoter (tetO), which is activated by the tetracycline-controlled transactivator protein (tTA). SNCA*A53T mice were crossed with tTA expressing mice to generate a strain that overexpresses alpha-synuclein mutant protein in the hippocampus and forebrain. This transgenic strain is referred to herein as α-syn*A53T.

Figure 9Q:
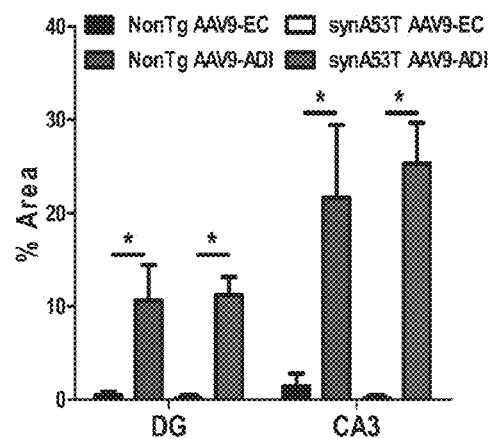
FIGS. 9A-D shows HA expression in non-transgenic and α-syn*A53T mice injected with AAV-EC and AAV-ADI. Results are quantified in FIG. 9Q.
FIGS. 9E-H show NeuN staining. Results are quantified in FIG. 9R.
FIGS. 9I-L show total alpha synuclein staining. Results are quantified in FIG. 9S.
FIGS. 9M-P show phosphorylated alpha-synuclein staining. Results are quantified in FIG. 9T. Statistical analysis was performed using 1-way ANOVA with multiple comparisons and Fisher's LSD. n=7-9/group.
Figure 9R:
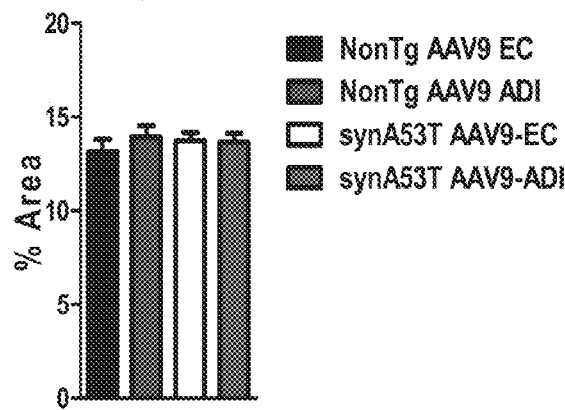
Figure 9S:
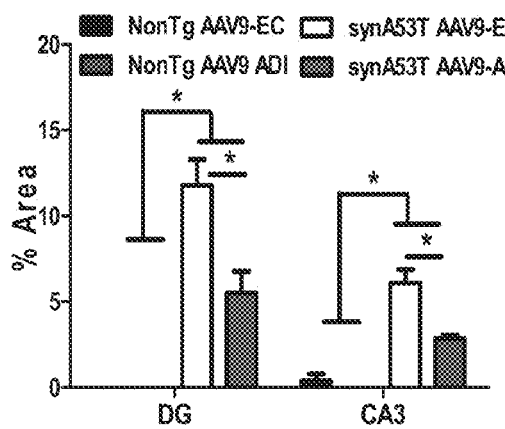
Figure 9T:
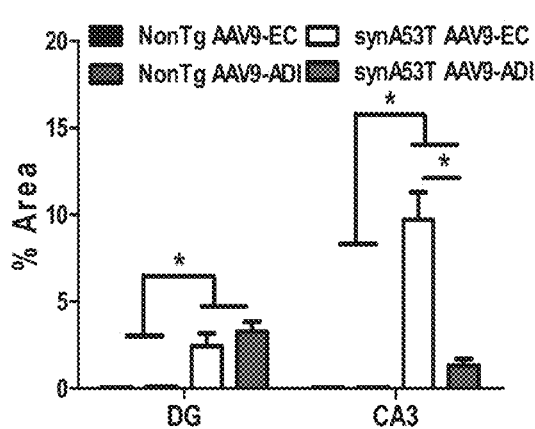

Experimental Design:

AAV9-ADI or AAV9-empty capsid (viral particle with no DNA) was injected into the CA3 region of the hippocampus of α-syn*A53T transgenic mice and non-transgenic littermates at 4 months of age. Viral expression was allowed for an additional 4 months. Brains were harvested after the 4-month duration and expression of the transgene was confirmed by immunohistochemistry. FIGS. 9B and 9D show positive staining for HA, indicating increased expression of ADI in non-transgenic mice and α-syn*A53T compared to AAV-EC injected controls.

Neuronal Integrity:

To assess potential adverse effects of treatment with ADI, neuronal integrity was assessed by staining with the neuronal marker NeuN. As shown in FIGS. 9E-H and 9R, levels of NeuN staining were not significantly different between treatment groups, suggesting no adverse effects of the ADI treatment in non-transgenic or α-syn*A53T mice.

Expression of α-Synuclein:

Levels of total α-synuclein and phosphorylated α-synuclein were assessed by immunohistochemistry. α-syn*A53T mice show significantly higher baseline levels of α-synuclein and phosphorylated α-synuclein compared to non-transgenic controls, suggesting increased α-synuclein deposition and pathology in the α-syn*A53T transgenic mice. Administration of AAV9-ADI significantly reduced total α-synuclein and phosphorylated α-synuclein area CA3 and the dentate gyrus of the hippocampus in α-syn*A53T mice. Reductions were not seen in mice injected with AAV-EC, suggesting that ADI overexpression is capable of reduce α-synuclein pathology in a mouse model of synucleinopathy.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method for reducing aggregation of a disordered protein in a subject, the method comprising administering to the subject a composition comprising arginine deiminase.

Clause 2. The method of clause 1, wherein the composition comprising arginine deiminase comprises a vector comprising a nucleotide sequence encoding an arginine deiminase.

Clause 3. The method of clause 2, wherein the nucleotide sequence encoding an arginine deiminase comprises the nucleotide sequence of SEQ ID NO: 1 or SEQ ID NO: 2.

Clause 4. The method of clause 1, wherein the composition decreases aggregation of a disordered protein without producing toxic levels of polyamines in the subject.

Clause 5. The method of clause 1, wherein the disordered protein is tau.

Clause 6. The method of clause 1, wherein the disordered protein is α-synuclein.

Clause 7. The method of clause 1, wherein the subject is human.

Clause 8. The method of clause 1, wherein the subject is diagnosed with or at risk of developing a disease characterized by aggregation of disordered protein.

Clause 9. The method of clause 8, wherein the disease characterized by aggregation of disordered protein is a tauopathy.

Clause 10. The method of clause 9, wherein the tauopathy is Alzheimer's disease, Huntington's disease, Pick's disease, primary age-related tauopathy, chronic traumatic encephalopathy, dementia pugilistica, progressive supranuclear palsy, corticobasal degeneration, frontotemporal dementia, parkinsonism linked to chromosome 17, Lytico-Bodig disease, ganglioglioma, gangliocytoma, meningioangiomatosis, tangle predominant dementia, postencephalitic parkinsonism, subacute scelrosing panencephalitis, lead encephalopathy, tuberous sclerosis, Hallervorden-Spatz disease, lipofuscinosis, argyrophilic grain disease, or frontotemporal lobar degeneration.

Clause 11. The method of clause 9, wherein the tauopathy is Alzheimer's disease.

Clause 12. The method of clause 8, wherein the disease characterized by aggregation of disordered protein is a synucleinopathy.

Clause 13. The method of clause 12, wherein the synucleinopathy is Parkinson's disease, dementia with Lewy bodies, or multiple system atrophy.

Clause 14. The method of clause 1, wherein the composition is administered parenterally.

Clause 15. The method of clause 1, further comprising encapsulating arginine deiminase in a vesicle prior to administration to the subject.

Clause 16. The method of clause 15, wherein the vesicle is selected from the group consisting of liposomes, niosomes, micelles, multilamellar vesicles, unilamellar vesicles, and polymersomes.

Clause 17. A method of treating a disease characterized by aggregation of disordered protein in a subject, the method comprising administering to the subject a composition comprising arginine deiminase.

Clause 18. The method of clause 17, wherein the composition comprising arginine deiminase comprises a vector comprising a nucleotide sequence encoding an arginine deiminase.

Clause 19. The method of clause 18, wherein the nucleotide sequence encoding an arginine deiminase comprises the nucleotide sequence of SEQ ID NO: 1 or SEQ ID NO: 2.

Clause 20. The method of clause 17, wherein the composition comprising arginine deiminase reduces aggregation of disordered protein without producing toxic levels of polyamines in the subject.

Clause 21. The method of clause 17, wherein the subject is human.

Clause 22. The method of clause 17, wherein the disease characterized by aggregation of disordered protein is a tauopathy.

Clause 23. The method of clause 22, wherein the tauopathy is Alzheimer's disease, Huntington's disease, Pick's disease, primary age-related tauopathy, chronic traumatic encephalopathy, dementia pugilistica, progressive supranuclear palsy, corticobasal degeneration, frontotemporal dementia, parkinsonism linked to chromosome 17, Lytico-Bodig disease, ganglioglioma, gangliocytoma, meningioangiomatosis, tangle predominant dementia, postencephalitic parkinsonism, subacute scelrosing panencephalitis, lead encephalopathy, tuberous sclerosis, Hallervorden-Spatz disease, lipofuscinosis, argyrophilic grain disease, or frontotemporal lobar degeneration.

Clause 24. The method of clause 22, wherein the tauopathy is Alzheimer's disease.

Clause 25. The method of clause 17, wherein the disease characterized by aggregation of disordered protein is a synucleinopathy.

Clause 26. The method of clause 25, wherein the synucleinopathy is Parkinson's disease, dementia with Lewy bodies, or multiple system atrophy.

Clause 27. The method of clause 17, wherein the composition is administered parenterally.

Clause 28. The method of clause 17, further comprising encapsulating arginine deiminase in a vesicle prior to administration to the subject.

Clause 29. The method of clause 28, wherein the vesicle is selected from the group consisting of liposomes, niosomes, micelles, multilamellar vesicles, unilamellar vesicles, and polymersomes.

What is claimed is:

1. A method of treating a tauopathy or a synucleinopathy characterized by aggregation of disordered protein in a subject, the method comprising parenterally administering to the subject a composition comprising arginine deiminase, wherein the composition comprising arginine deiminase comprises a vector comprising the polynucleotide sequence of SEQ ID NO: 2.

2. The method of claim 1, wherein the composition comprising arginine deiminase reduces aggregation of disordered protein without producing toxic levels of polyamines in the subject.

3. The method of claim 1, wherein the subject is human.

4. The method of claim 1, wherein the tauopathy is selected from Alzheimer's disease, Huntington's disease, Pick's disease, primary age-related tauopathy, chronic traumatic encephalopathy, dementia pugilistica, progressive supranuclear palsy, corticobasal degeneration, frontotemporal dementia, parkinsonism linked to chromosome 17, Lytico-Bodig disease, ganglioglioma, gangliocytoma, meningioangiomatosis, tangle predominant dementia, postencephalitic parkinsonism, subacute scelrosing panencephalitis, lead encephalopathy, tuberous sclerosis, Hallervorden-Spatz disease, lipofuscinosis, argyrophilic grain disease, frontotemporal lobar degeneration, or a combination thereof.

5. The method of claim 4, wherein the tauopathy is Alzheimer's disease.

6. The method of claim 1, wherein the synucleinopathy is selected from Parkinson's disease, dementia with Lewy bodies, or multiple system atrophy, or a combination thereof.

7. The method of claim 1, wherein the vector is an adeno-associated virus (AAV) vector.

8. The method of claim 7, wherein the AAV vector is an AAV9 vector.

* * * * *

SEQUENCE LISTING

```
<160> NUMBER OF SEQ ID NOS: 5

<210> SEQ ID NO 1
<211> LENGTH: 1233
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1233)
<223> OTHER INFORMATION: Bacterial arginine deiminase

<400> SEQUENCE: 1
atgtctgtat ttgacagtaa atttaaagga attcacgttt attcagaaat tggtgaatta     60
gaatcagttc tagttcacga accaggacgc gaaattgact atattacacc agctagacta    120
gatgaattat tattctcagc tatcttagaa agccacgatg ctagaaaaga acacaaacaa    180
ttcgtagcag aattaaaagc aaacgacatc aatgttgttg aattaattga tttagttgct    240
gaaacatatg atttagcatc acaagaagct aaagataaat taatcgaaga atttttagaa    300
gactcagaac cagttctatc agaagaacac aaagtagttg taagaaactt cttaaaagct    360
aaaaaaacat caagaaaatt agtagaaatc atgatggcag ggatcacaaa atacgattta    420
ggtatcgaag cagatcacga attaatcgtt gacccaatgc caaacctata cttcacacgt    480
gacccatttg catcagtagg taatggtgta acaatccact acatgcgtta caaagttaga    540
caacgtgaaa cattattctc aagatttgta ttctcaaatc accctaaact aattaacact    600
ccatgatact acgacccttc actaaaatta tcaatcgaag gtggagacgt atttatctac    660
aacaatgaca cattagtagt tggtgtttct gaaagaactg acttacaaac agttacttta    720
ttagctaaaa acattgttgc taataaagaa tgtgaattca aacgtattgt tgcaattaac    780
gttccaaaat gaacaaactt aatgcactta gacacatgac taacaatgtt agacaaggac    840
aaattcctat actcaccaat cgctaacgac gtatttaaat tctgagatta tgacttagta    900
aacggtggag cagaaccaca accagttgaa aacggattac ctctagaagg attattacaa    960
```

| | |
|---|---|
| tcaatcatta acaaaaaacc agttttaatt cctatcgcag gtgaaggtgc ttcacaaatg | 1020 |
| gaaatcgaaa gagaaacaca cttcgatggt acaaactact tagcaattag accaggtgtt | 1080 |
| gtaattggtt actcacgtaa cgaaaaaaca aacgctgctc tagaagctgc aggcattaaa | 1140 |
| gttcttccat tccacggtaa ccaattatca ttaggtatgg gtaacgctcg ttgtatgtca | 1200 |
| atgcctttat cacgtaaaga tgttaagtga tag | 1233 |

<210> SEQ ID NO 2
<211> LENGTH: 1230
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1230)
<223> OTHER INFORMATION: Mammalianized arginine deiminase

<400> SEQUENCE: 2

| | |
|---|---|
| atgtcggtgt ttgattcaaa gttcaaagga atccacgtgt actcagaaat tggcgagctc | 60 |
| gaaagcgtgc tggtgcacga acccggaaga gagatcgact atatcactcc agcgcgcctg | 120 |
| gatgaactgc tgttctcggc catcttggaa tcgcatgacg cacgcaagga acacaagcaa | 180 |
| tttgtcgccg aacttaaagc caatgacatc aatgtggtcg aactgattga cctggtcgcg | 240 |
| gaaacctacg atctggcgag ccaggaagcc aaagataagc tcatcgagga gttttggag | 300 |
| gacagcgaac cagtgctctc cgaagaacat aaggtcgtgg tgaggaattt cctcaaagct | 360 |
| aaaaagactt cccggaagct ggtggagatt atgatggctg gcatcaccaa atacgatctt | 420 |
| ggcatcgagg ccgaccacga gctgatcgtc gatcctatgc cgaatctgta ctttacccgc | 480 |
| gaccccttcg cctcggtcgg aaatggggtg actatccact acatgcgcta caaagtcaga | 540 |
| caacgggaaa ccctcttctc ccggttcgtg ttctccaacc atccgaagct gatcaacacc | 600 |
| ccttggtact acgaccccatc actgaagctc tccatcgaag gcggtgacgt gttcatctac | 660 |
| aacaatgata ccctcgtggt gggcgtgtca gagcggaccg acttgcaaac tgtgacccc tt | 720 |
| ctggctaaga acatcgtggc aaacaaagag tgcgagttca gcgcatcgt cgctatcaac | 780 |
| gtcccgaagt ggacgaacct catgcaccct gacacctggc tgacgatgtt ggacaaagac | 840 |
| aagttcctct actccccgat tgcaaacgat gtgttcaagt ttgggattac gacttggtg | 900 |
| aacggaggag ccgagccaca gccagtggag aacggactgc ccctcgaagg actgctgcag | 960 |
| agcatcatca caagaagcc tgtgctgatc ccgatcgccg gagagggagc cagccagatg | 1020 |
| gaaattgagc gggagactca tttcgatggg actaactacc tggccatcag ccgggcgtg | 1080 |
| gtgattggat atagcaggaa cgaaaagact aatgcagcgt ggaagcggc aggaatcaag | 1140 |
| gtcctgccgt tccacggaaa tcagctttcg ctcggtatgg ggaacgcgag atgtatgtcg | 1200 |
| atgccgctgt cccgcaagga cgtgaagtgg | 1230 |

<210> SEQ ID NO 3
<211> LENGTH: 1302
<212> TYPE: DNA
<213> ORGANISM: Artificial Sequence
<220> FEATURE:
<223> OTHER INFORMATION: Synthetic

<400> SEQUENCE: 3

| | |
|---|---|
| aagctgaccg gtgccgccac catgtcggtg tttgattcaa agttcaaagg aatccacgtg | 60 |

| | | |
|---|---|---|
| tactcagaaa ttggcgagct cgaaagcgtg ctggtgcacg aacccggaag agagatcgac | 120 | |
| tatatcactc cagcgcgcct ggatgaactg ctgttctcgg ccatcttgga atcgcatgac | 180 | |
| gcacgcaagg aacacaagca atttgtcgcc gaacttaaag ccaatgacat caatgtggtc | 240 | |
| gaactgattg acctggtcgc ggaaacctac gatctggcga gccaggaagc caaagataag | 300 | |
| ctcatcgagg agttttttgga ggacagcgaa ccagtgctct ccgaagaaca taaggtcgtg | 360 | |
| gtgaggaatt tcctcaaagc taaaaagact tcccggaagc tggtggagat tatgatggct | 420 | |
| ggcatcacca atacgatct tggcatcgag gccgaccacg agctgatcgt cgatcctatg | 480 | |
| ccgaatctgt actttacccg cgacccccttc gcctcggtcg gaaatggggt gactatccac | 540 | |
| tacatgcgct acaaagtcag acaacgggaa accctcttct cccggttcgt gttctccaac | 600 | |
| catccgaagc tgatcaacac cccttggtac tacgacccat cactgaagct ctccatcgaa | 660 | |
| ggcggtgacg tgttcatcta caacaatgat accctcgtgg tgggcgtgtc agagcggacc | 720 | |
| gacttgcaaa ctgtgaccct tctggctaag aacatcgtgg caaacaaaga gtgcgagttc | 780 | |
| aagcgcatcg tcgctatcaa cgtcccgaag tggacgaacc tcatgcacct tgacacctgg | 840 | |
| ctgacgatgt tggacaaaga caagttcctc tactccccga ttgcaaacga tgtgttcaag | 900 | |
| ttttgggatt acgacttggt gaacggagga gccgagccac agccagtgga aacggactg | 960 | |
| cccctcgaag gactgctgca gagcatcatc aacaagaagc ctgtgctgat cccgatcgcc | 1020 | |
| ggagagggag ccagccagat ggaaattgag cgggagactc atttcgatgg gactaactac | 1080 | |
| ctggccatca gaccgggcgt ggtgattgga tatagcagga acgaaaagac taatgcagcg | 1140 | |
| ttggaagcgg caggaatcaa ggtcctgccg ttccacggaa atcagctttc gctcggtatg | 1200 | |
| gggaacgcga gatgtatgtc gatgccgctg tcccgcaagg acgtgaagtg gatggcctca | 1260 | |
| tcctacccctt acgatgtccc ggactacgct atgtgagcta gc | 1302 | |

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
aagctgaccg gtgccgccac c        21

<210> SEQ ID NO 5
<211> LENGTH: 424
<212> TYPE: PRT
<213> ORGANISM: Artificial Sequence
<220> FEATURE:
<223> OTHER INFORMATION: Synthetic

<400> SEQUENCE: 5

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

```
Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Lys Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp Met Ala Ser Ser Tyr Pro
                405                 410                 415

Tyr Asp Val Pro Asp Tyr Ala Met
            420
```